(12) United States Patent
Chen

(10) Patent No.: US 10,383,577 B2
(45) Date of Patent: Aug. 20, 2019

(54) PORTABLE SENSING AND OPERATIONAL DEVICE

(71) Applicant: HUAFAN UNIVERSITY, New Taipei (TW)

(72) Inventor: Kang-Ying Chen, New Taipei (TW)

(73) Assignee: Huafan University, New Taipei (TW)

( * ) Notice: Subject to any disclaimer, the term of this patent is extended or adjusted under 35 U.S.C. 154(b) by 333 days.

(21) Appl. No.: 14/708,367

(22) Filed: May 11, 2015

(65) Prior Publication Data

US 2016/0058384 A1    Mar. 3, 2016

(30) Foreign Application Priority Data

Aug. 29, 2014  (TW) .............................. 103130044 A

(51) Int. Cl.
*A61B 5/00*   (2006.01)
*A61B 5/024*  (2006.01)
*A61B 5/0404* (2006.01)
*A61B 5/0476* (2006.01)

(52) U.S. Cl.
CPC .......... *A61B 5/6898* (2013.01); *A61B 5/0024* (2013.01); *A61B 5/02416* (2013.01); *A61B 5/0404* (2013.01); *A61B 5/0476* (2013.01)

(58) Field of Classification Search
CPC . A61B 5/6898; A61B 5/02416; A61B 5/0476; A61B 5/0404
USPC ......................................................... 702/196
See application file for complete search history.

(56) References Cited

U.S. PATENT DOCUMENTS

| 2012/0101781 A1* | 4/2012 | Chen ...................... G06F 17/14 |
| | | 702/189 |
| 2013/0033451 A1* | 2/2013 | Olson ..................... G06F 3/044 |
| | | 345/174 |
| 2016/0041645 A1* | 2/2016 | Ray ...................... G06F 3/0418 |
| | | 345/174 |

* cited by examiner

*Primary Examiner* — Anthony Ho
(74) *Attorney, Agent, or Firm* — Rosenberg, Klein & Lee

(57) ABSTRACT

The present invention provides a portable sensing and operational device, which uses a sensing module to receive the sensing signal transmitted by the sensor and produce a sensing datum correspondingly. Then an operational circuit operates a first matrix and a second matrix according to the sensing datum. The first matrix corresponds to a plurality of maximum values; the second matrix corresponds to a plurality of minimum values. The operational circuit operates to generate at least a component by decomposing the first matrix and the second matrix. The component is provided to an output circuit for outputting the component to an electronic device.

11 Claims, 4 Drawing Sheets

PORTABLE SENSING AND OPERATIONAL DEVICE

FIELD OF THE INVENTION

The present invention relates generally to an analyzing device, and particularly to a portable sensing and operational device.

BACKGROUND OF THE INVENTION

Early instruments for measuring physiological signals, such as sphygmomanometers, blood glucose meters, and heart monitors, are bulky, making them uneasy to be moved. Thereby, it is difficult for testees to carry these measurement instruments. Then, once the testees move, such as leaving home, medical personnel are hard to know the health status of the testees, leading to a risky period of home care. Accordingly, portable measurement instruments with corresponding portable consumables are provided by various manufacturers of measurement instruments for physiological signals.

The portable design is focused on measuring the physiological signal of a testee, not considering uploading the measurement results of the physiological signals to a remote database system. Thereby, the measurement results of the physiological signals by theses instruments will only be displayed on their respective display unit, such as the liquid-crystal display of a sphygmomanometer. In the current caring environment, the measurements results of the physiological signals as described above, for example, the systolic and diastolic pressure values, can be transmitted to medical or nursing institutions only by manual phone calls or facsimiles of caregivers or family members. In other words, the operation of transmitting the measurement results of physiological signals to data management institutions or nursing institutions is still done manually and thus inefficiently.

Accordingly, some manufacturers further include wireless network modules in the instruments for collecting physiological signals. By connecting a monitoring device for physiological signals outside the body, the physiological signals of the monitored patient can be extracted periodically. Then, the physiological signal data acquired by monitoring the patient are sent to the external monitoring center via the wireless network module and used as the reference for analyzing the patient's condition.

In the current environment of information explosion, people can acquire biomedical information through the network or television media with ease. They naturally want to get the monitoring results of monitoring instruments real-timely. Nonetheless, the data quantity of general monitoring results to be analyzed is extremely large and not affordable by general portable equipment.

Summing up the problems as described above, the present invention provides a portable sensing and operational device. A portable operational circuit operates the sensing data corresponding to the sensing signal and generates a component, which is provided to the electronic device connected externally for displaying the corresponding graphs of the sensing data. Consequently, people can get the biomedical monitoring results real-timely. For example, they can use a cell phone to execute an application program of graphs for viewing the variation of blood pressure or the heart rate variability.

SUMMARY

An objective of the present invention is to provide a portable sensing and operational device, which provides portable operations capable of operating the monitoring results without uploading to a computer device.

The present invention provides a portable sensing and operational device, which comprises a sensing module, an operational circuit, and an output circuit. The sensing circuit is connected electrically to at least a sensor for receiving the sensing signal transmitted by the sensor and producing at least a sensing datum correspondingly. The operational circuit is connected electrically to the sensing module. It acquires a plurality of maximum values and a plurality of minimum values according to the sensing data and operates a first matrix and a second matrix according to the plurality of maximum values and the plurality of minimum values. Then it operates to generate at least a component according to the first matrix and the second matrix. The component is provided to the output circuit for outputting to an electronic device connected externally.

DETAILED DESCRIPTION

In order to make the structure and characteristics as well as the effectiveness of the present invention to be further understood and recognized, the detailed description of the present invention is provided as follows along with embodiments and accompanying figures.

Figure 1:
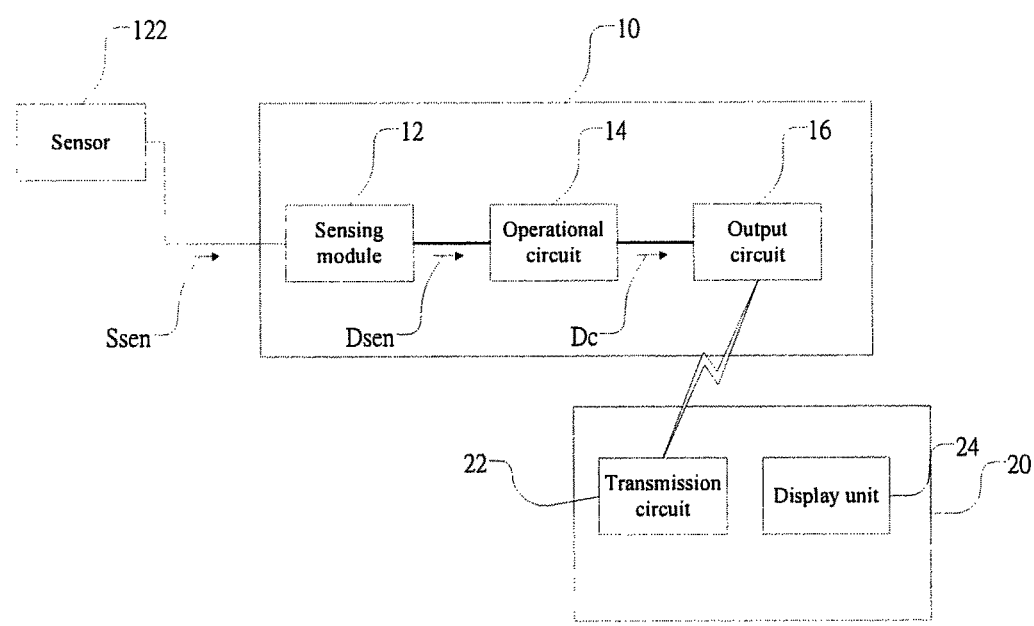
FIG. 1 shows a block diagram according to a preferred embodiment of the present invention.
Figure 2:
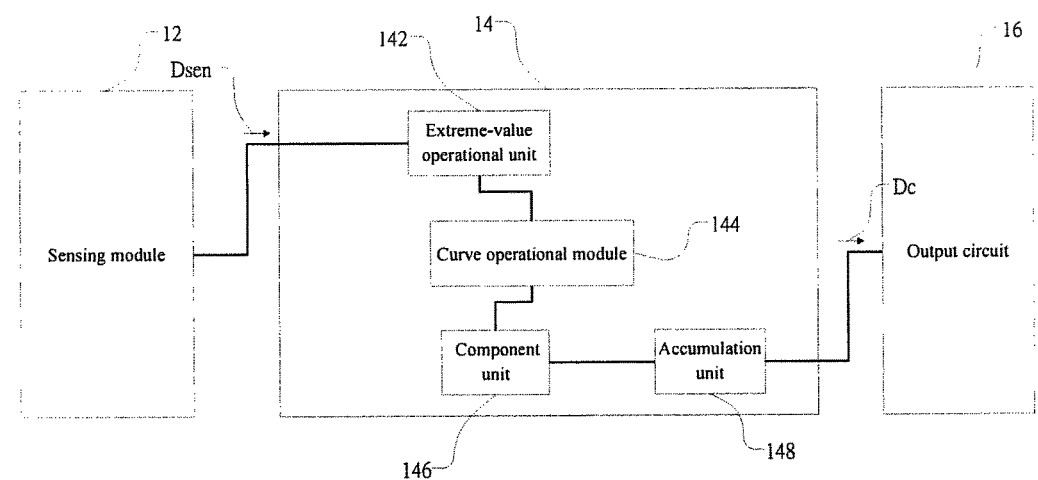
FIG. 2 shows a block diagram of the operational circuit according to a preferred embodiment of the present invention.

Please refer to FIG. 1 and FIG. 2, which show a block diagram according to a preferred embodiment of the present invention and a block diagram of the operational circuit according to a preferred embodiment of the present invention. As shown in the figures, the portable sensing and operational device 10 according to the present invention comprises a sensing module 12, an operational circuit 14, and an output circuit 16. The operational circuit 14 comprises an extreme-value operational unit 142, a curve operational module 144, a component unit 146, and an accumulation unit 148.

The sensing module 12 is connected electrically to at least a sensor 122. It receives the sensing signal Ssen transmitted by the sensor 122 and produces at least a sensing datum Dsen. The sensing signal Ssen and the sensing data Dsen according to the present embodiment are transmitted serially. This is because the sensing signal Ssen and the sensing data Dsen are serial sensing signal and serial sensing data, respectively. Nonetheless, the present invention is not limited to serial transmission. The sensing signal Ssen and the sensing data Dsen can further be parallel sensing signal and parallel sensing data transmitted in parallel. The operational circuit 14 is connected electrically to the sensing module 12. It acquires a plurality of maximum values and a plurality of minimum values according to the sensing data Dsen and operates to generate a first matrix and a second matrix correspondingly according to the plurality of maximum values and the plurality of minimum values. The operational circuit 14 decomposes the first matrix and the second matrix into a plurality of first sub-matrices and a plurality of second sub-matrices, respectively, for calculating at least a corresponding average-value curve of the plurality of maximum values and the plurality of minimum values. The operational circuit 14 calculates to generate at least a component according to the average-value curve and the sensing data Dsen. The output circuit 16 is connected electrically to the operational circuit 14 and outputs the component to an electronic device 20 according to the sensing data Dsen. The electronic device 20 receives the component transmitted by the output circuit 16 via the transmission circuit 22. The electronic device 20 displays a graph on a display unit 24 of the electronic device 20 according to the component.

As shown in FIG. 2, the extreme-value operational unit 142 receives the sensing data Dsen output by the sensing module 12 and acquires the plurality maximum vales and the plurality of minimum values according to the sensing data Dsen. The curve operational module 144 constructs the first matrix and the second matrix according to the plurality of maximum values and the plurality of minimum values acquired by the extreme-value operational unit 142, respectively. The curve operational module 144 decomposes the matrices into the plurality of first sub-matrices and the plurality of second sub-matrices, respectively. In addition, the curve operational module 144 calculates to generate the average-value curve corresponding to the plurality of maximum values and the plurality of minimum values according to the plurality of sub-matrices. The product of the plurality of first sub-matrices is equal to the first matrix; the product of the plurality of second sub-matrices is equal to the second matrix. The plurality of sub-matrices are selected from the group consisting of a plurality of triangular matrices, a plurality of orthogonal matrices, a unit matrix, a diagonal matrix.

The curve operational module 144 according to the present embodiment adopts an envelope method. Hence, the curve operational module 144 constructs the first matrix and the second matrix according to the plurality of maximum values and the plurality of minimum values, respectively. Then the first and second matrices are used for generating a maxima envelope and a minima envelope, which are used for calculations and generating a plurality of interpolation values corresponding to the plurality of maximum values and a plurality of interpolation values corresponding to the plurality of minimum values, respectively. The maxima envelope corresponds to the plurality of maximum values and the plurality of first interpolation values; the minima envelope corresponds to the plurality of minimum values and the plurality of second interpolation values. Then, the average-value curve is generated according to the plurality of maximum values, the plurality of minimum values, the plurality of first interpolation values, and the plurality of second interpolation values. Next, the component unit 146 generates the component according to the average-value curve and the input data. The operational circuit 14 according to the present embodiment further accumulates the component output by the component unit 146 by using the accumulation unit 148 and producing an accumulated component. An average-value component is then calculated according to the accumulated component.

The output circuit 16 receives the operational result Dc output by the operational circuit 14, namely, the component produced by the component unit or the average-value component produced by the accumulation unit 148. Please refer again to FIG. 1. The output circuit 16 is connected electrically to the electronic device 20. The electrical connection to the electronic device 20 can be done by using a transmission line. For example, the output circuit 16 supports the universal serial bus (USB), the RS-232 transmission protocol, or the RS-485 transmission protocol. Thereby, the output circuit 16 transmits the operational result Dc of the operational circuit 14 to the electronic device 20 via a USB transmission, an RS-232 transmission line, or an RS-485 transmission line. The output circuit 16 can also transmit the operational result Dc of the operational circuit 14 to the electronic device 20 via the wireless transmission interface. For example, the output circuit 16 transmits the operational result Dc of the operational circuit 14 to the electronic device 20 via the Wi-Fi transmission protocol or the Bluetooth transmission protocol.

Figure 3:
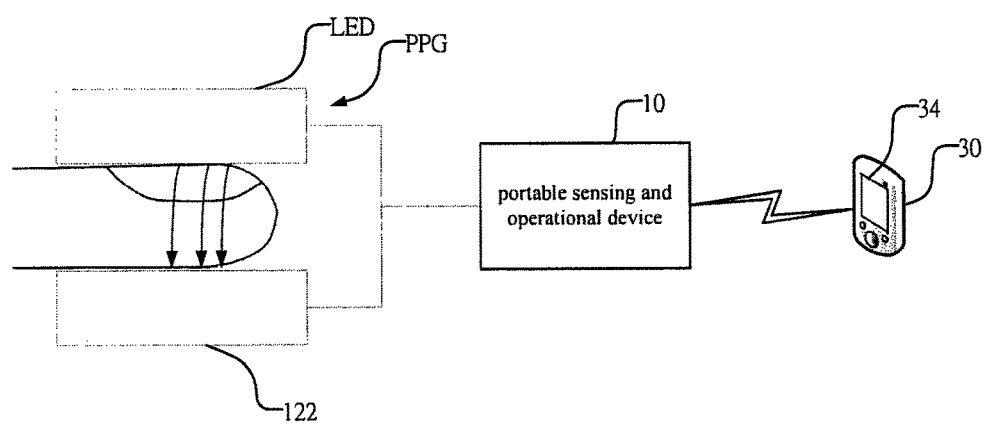
FIG. 3 shows a structural schematic diagram according to another preferred embodiment of the present invention.

Moreover, the sensor 122 according to the present invention can be a photoplethysmography (PPG) sensor for extracting physiological signals. The PPG requires an LED as the light source and a photo-receiving transistor as the major structure for PPG measurement. In addition, it is based on the measuring the characteristics of light in the selected block of skin. In general, after illuminating light into the skin and as the light propagates in biological tissues, the light will be absorbed by various materials such the skin color, bones, and blood in arteries and veins. During the contraction period of heart, the absorption of light is increased in arteries because the substance that absorbs light, namely, the hemoglobin, is increased substantially and the light path in arteries is increased. This kind of graph receiving light signals varying with time and tissues is called the PPG. As shown in FIG. 3, the portable sensing and operational device 10 is connected electrically to the PPG sensor PPG, which comprises a light source LED and the sensor 122. Then the portable sensing and operational device 10 can sense the pulsing phenomenon of arteries using the sensor 122 in the light absorption process and provide the operational result Dc to the smartphone 30. The smartphone 30 executes an application program (APP) for analyzing cardiovascular parameters and displaying the corresponding graphs.

Figure 4:
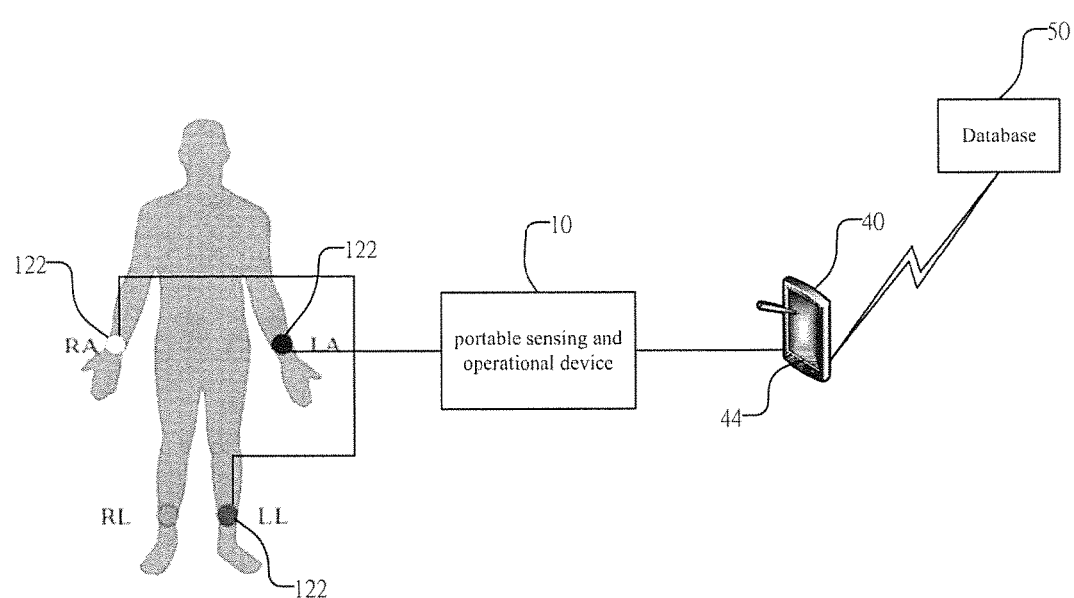
FIG. 4 shows a structural schematic diagram according to another preferred embodiment of the present invention.

Alternatively, the sensor 122 can be used as an electrocardiograph sensor. In general, a simplified electrocardiograph can be obtained by disposing at least three leads, namely, three electrodes. As shown in FIG. 4, the sensor 122 is disposed at the left hand, the right hand, and the left leg for forming voltage differences between the left and right hands, the left hand and the left leg, and the right hand and the left leg. The voltage differences are transmitted to the portable sensing and operational device 10 and then to a tablet computer 40 through a transmission line. The tablet computer 40 executes an application program (APP) for further analyses and operations. Afterwards, the operational result Dc of the electrocardiograph is uploaded to the database 50 for subsequent medical analysis and tracing or displaying. Furthermore, the present invention can be applied to sensing electroencephalogram.

In addition to the application of physiological signals as described above, the present invention can be further applied to applications of sensing signals such as sensing sound, reading sound tracks, sensing mechanical vibrations, sensing wireless electromagnetic waves, and sensing electroencephalogram. The sensing module 12 converts the sensing signal Ssen to the sensing data Dsen. Accordingly, the operational circuit acquires the maximum value and the minimum value. Then the operational circuit acquires the first matrix and the second matrix by means of the maximum and minimum values. The first and second matrices are decomposed and operated to generate the average-value curve, which is further operated to generate the component for the output circuit. The output circuit outputs the component to the electronic device, which displays the corresponding graph or performs further analyses and operations. Next, the analyzed operational result Dc is uploaded to a database. Alternatively, the electronic device will display the operational result Dc such as "the sensing result is OK".

To sum up, the portable sensing and operational device according to the present invention uses the sensing module to receive the sensing signal transmitted by the sensor and produce the corresponding sensing data. The operational circuit calculates the sensing data to generate the operational result Dc, which is provided to the external electronic device for displaying graphs. Without relying on external computer device for operating the sensing data, the real-time sensing result can be acquired.

Accordingly, the present invention conforms to the legal requirements owing to its novelty, nonobviousness, and utility. However, the foregoing description is only embodiments of the present invention, not used to limit the scope and range of the present invention. Those equivalent changes or modifications made according to the shape, structure, feature, or spirit described in the claims of the present invention are included in the appended claims of the present invention.

The invention claimed is:

1. A portable sensing and operational device, comprising:
   a sensing module, connected electrically to at least a sensor, receiving a sensing signal transmitted by said sensor, and producing at least a sensing datum according to said sensing signal, said sensor sensing a physiological monitoring signal to generate said sensing datum;
   an operational circuit, connected electrically to said sensing module, receiving a plurality of maximum values and a plurality of minimum values according to said sensing datum, generating at least an average-value curve corresponding to said plurality of maximum values and said plurality of minimum values, operating said average-value curve and said sensing datum to generate at least a component, and generating an operational result according to said component, wherein said operational result is related to a cardiovascular parameter; and
   an output circuit, connected electrically to said operational circuit, and transmitting said operational result to an electronic device according to said sensing datum;
   wherein said sensor is a photoplethysmography (PPG) sensor for extracting said physiological monitoring signal.

2. The portable sensing and operational device of claim 1, wherein said operational circuit comprises:
   an extreme-value operational unit, receiving said sensing datum, and acquiring said plurality of maximum values and said plurality of minimum values according to said sensing datum;
   a curve operational module, operating to generate said average-value curve corresponding to said plurality of maximum values and said plurality of minimum values; and
   a component unit, generating said component according to said average-value curve and said sensing datum.

3. The portable sensing and operational device of claim 2, wherein said extreme-value operational unit, said curve operational module, and said component unit are integrated into an integrated circuit.

4. The portable sensing and operational device of claim 1, wherein said component corresponds to a frequency of said sensing signal.

5. The portable sensing and operational device of claim 1, wherein said output circuit is connected to said electronic device via a transmission line.

6. The portable sensing and operational device of claim 5, wherein said transmission line supports the universal serial bus transmission protocol, the RS-232 transmission protocol, or the RS-485 transmission protocol.

7. The portable sensing and operational device of claim 1, wherein said output circuit is connected to said electronic device via a wireless transmission interface.

8. The portable sensing and operational device of claim 7, wherein said wireless transmission interface supports the Bluetooth transmission protocol or the Wi-Fi transmission protocol.

9. The portable sensing and operational device of claim 1, wherein said electronic device executes an application program for converting said component into a graph.

10. The portable sensing and operational device of claim 1, wherein said electronic device executes an application program for analyzing said component and producing an operational result.

11. The portable sensing and operational device of claim 1, further including forming a first matrix and a second matrix respectively including said plurality of maximum values and said plurality of minimum values, decomposing said first matrix and said second matrix into a plurality of first sub-matrices and a plurality of second sub-matrices representing maxima and minima envelopes, said average-value curve generated based on said pluralities of first sub-matrices and second sub-matrices.

* * * * *